United States Patent [19]

Brucker et al.

[11] Patent Number: 5,423,805
[45] Date of Patent: Jun. 13, 1995

[54] LASER CATHETER WITH MOVEABLE INTEGRAL FIXATION WIRES

[75] Inventors: Gregory G. Brucker, Minneapolis; Steven D. Savage, Brooklyn Center, both of Minn.

[73] Assignee: Angeion Corporation, Plymouth, Minn.

[21] Appl. No.: 32,473

[22] Filed: Mar. 15, 1993

Related U.S. Application Data

[63] Continuation of Ser. No. 831,539, Feb. 5, 1992, abandoned.

[51] Int. Cl.⁶ ............................................. A61B 17/36
[52] U.S. Cl. ............................................. 606/15; 606/7; 606/16
[58] Field of Search ............ 606/2, 3, 7-17; 128/772, 657, 395-398; 604/170, 95

[56] References Cited

U.S. PATENT DOCUMENTS

| | | | |
|---|---|---|---|
| 3,858,577 | 1/1975 | Bass et al. | 606/15 X |
| 4,592,353 | 6/1986 | Daikuzono | 606/16 |
| 4,785,815 | 11/1988 | Cohen | 606/7 X |
| 4,832,024 | 5/1989 | Boussignac et al. | 606/7 |
| 4,834,093 | 5/1989 | Littleford | 606/7 |
| 4,844,062 | 7/1989 | Wells | 606/7 |
| 4,985,028 | 1/1991 | Isner et al. | 606/15 |
| 4,997,431 | 3/1991 | Isner et al. | 606/15 |
| 5,003,990 | 4/1991 | Osypka | 128/772 |
| 5,026,367 | 6/1991 | Leckrone et al. | 606/7 |
| 5,041,121 | 8/1991 | Wondrazek et al. | 606/15 X |
| 5,053,033 | 10/1991 | Clarke | 606/7 X |
| 5,193,526 | 3/1993 | Daikuzono | 606/16 X |

FOREIGN PATENT DOCUMENTS

| | | | |
|---|---|---|---|
| 27632 | 4/1981 | European Pat. Off. | 606/15 |
| 3617019 | 11/1987 | Germany | 606/15 |

*Primary Examiner*—Peter A. Aschenbrenner
*Attorney, Agent, or Firm*—Patterson & Keough

[57] ABSTRACT

A laser catheter for irradiation of human myocardial tissue containing a movable feedback mechanism for monitoring the damage created by laser irradiation, and which is usable with standard catheters designed for angiography and angioplasty. Means for sensing distal temperature are provided in the form of a plurality of movable thermocouples, along with the ability to cool the fiber optic and distal tip with a flushing solution. Flushing of the area adjacent to the tip is provided for by a fluid which travels the length of the laser catheter.

16 Claims, 6 Drawing Sheets

LASER CATHETER WITH MOVEABLE INTEGRAL FIXATION WIRES

CROSS REFERENCES TO CO-PENDING APPLICATIONS

U.S. patent application Ser. No. 07/608,281, filed Nov. 2, 1990, and U.S. patent application Ser. No. 07/608,290, filed Nov. 2, 1990, are commonly assigned to the assignee of the present invention. This application is a continuance of Ser. No. 07/831,539, now abandoned, filed Feb. 5, 1992.

BACKGROUND OF THE INVENTION

1. Field of the Invention

The present invention pertains to a medical device for use in therapy of a patient, and more particularly, pertains to a catheter for use in association with laser irradiation.

2. Description of the Prior Art

It is known in the art to use laser energy for medical purposes. A common medical application is in the ablation of tissue. For external use, the laser energy may be directly applied. However, when the procedure requires ablation of tissue which is not readily accessible, the use of a laser catheter is common. A typical application for a laser catheter is in the cardiovascular system. U.S. Pat. Nos. 4,997,431 and 4,985,028, both issued to Isner et al., show laser catheters particularly adapted for laser ablation within the cardiovascular system.

It is convenient to utilize a guide wire and or fixation wire in accordance with positioning and maintaining position of an ablation catheter. The above referenced patents issued to Isner et al., and incorporated herein by reference, teach the use of a wire for those purposes.

The ablation of tissue must be accomplished with great precision as the danger of also ablating necessary adjacent tissue is always present, especially when the process occurs remotely at the distal end of a relatively long catheter. U.S. Pat. No. 4,785,806 issued to Deckelbaum discusses a system whereby an attempt is made to distinguish different types of tissue using ultraviolet fluoroscopy. A similar approach is proposed in U.S. Pat. No. 4,718,417 issued to Kittrell et al. Spectral analysis of reflected light energy is also proposed in U.S. Pat. No. 4,669,467 issued to Willett et al.

However, none of these approaches monitors the operation of the ablation activity itself. It is the production and absorption of electromagnetic radiation producing controlled heating which actually ablates the unwanted tissue. The prior art discusses distinguishing the tissue prior to ablation and analyzing the products of the procedure following ablation, but none of the references measures the ablation activity directly during the heating process.

SUMMARY OF THE INVENTION

The present invention overcomes the disadvantages of the prior art by providing an ablation catheter system which utilizes a guiding/fixation wire having temperature monitoring sensors located at the distal tip. In this manner, maximum use of the cross-sectional area of the catheter body is obtained.

The general purpose of the present invention is to provide a laser catheter with a movable integral guidance/fixation wire including temperature sensing means, cooling means and flushing means.

According to one embodiment of the present invention, there is provided a catheter where a central lumen consists of a plastic tube approximately 100 cm long to which is affixed at its distal end a metallic or plastic tip. The tip consists of two components: one is a central lumen for placement and fixation of a single optical fiber, and the second is a lumen through which a mutually attached and movable stiffener wire and wires coupled to temperature sensors laterally pass. Multiple temperature sensors, such as thermocouples, are affixed along and near the end of the mutually attached stiffener wire. This provides thermocouples which are movable with respect to the tip. The thermocouples are designed such that they are electrically isolated from the stiffener wire and serve as one of two bipolar sensing electrodes, the other electrode being the tip itself.

Where heart tissue is involved, bipolar mapping can be carried out by measuring local activation potentials of the endocardial surface. In conjunction with standard EP monitoring equipment, the signals generated can be used to determine electrophysiological properties of the tissue that lies between the electrodes. During ablation, the signals can be watched for changes.

Having thus described the embodiments of the present invention, it is the principal object hereof to provide a laser catheter with a movable integral guidance/fixation wire including temperature sensing means, cooling means and flushing means.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
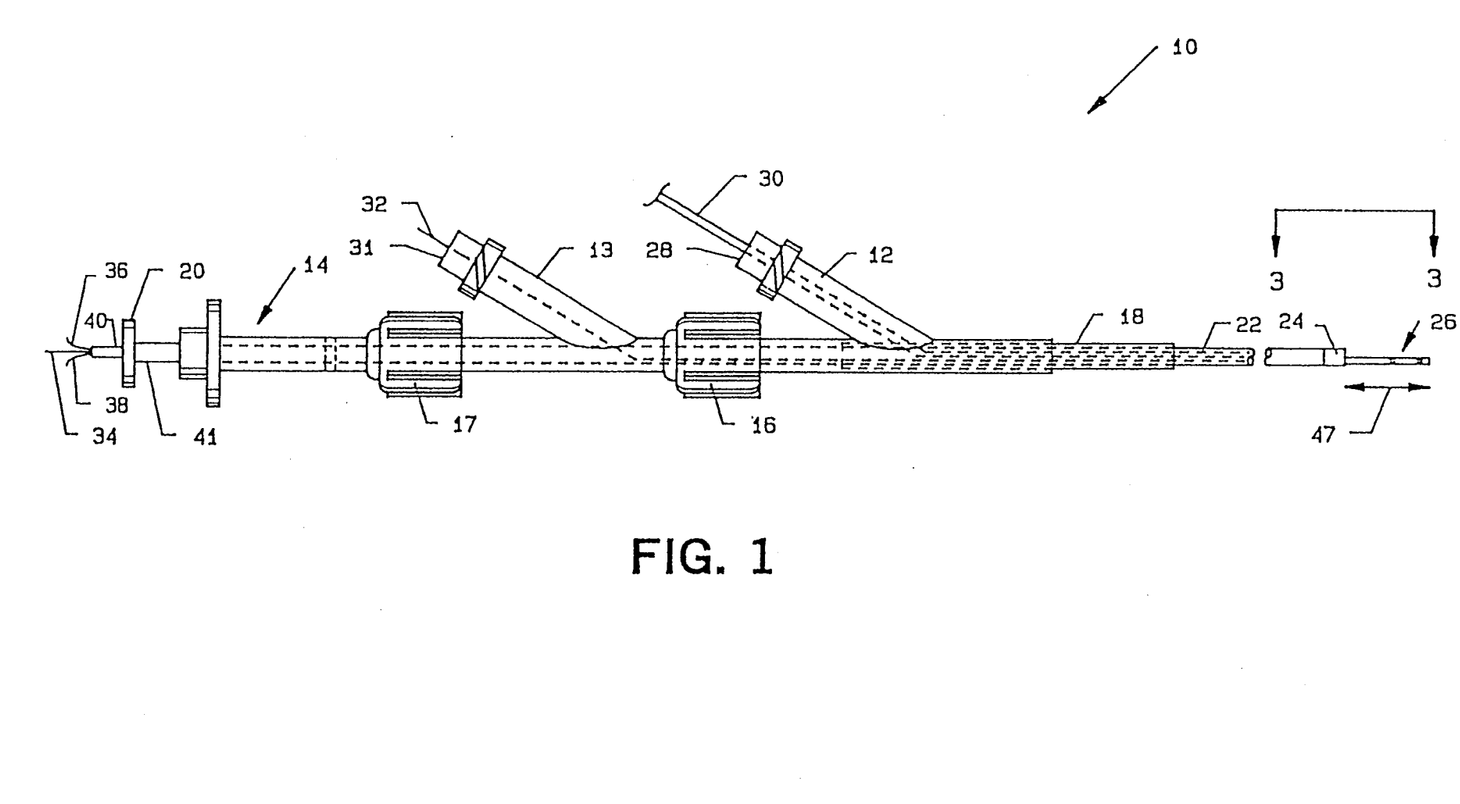
FIG. 1 illustrates a plan view of a movable integral fixation wire laser catheter, the present invention.

FIG. 1 illustrates a plan view of an integral fixation wire laser catheter 10. The laser catheter 10 includes Y-connectors 12 and 13 and a syringe 14 coupled to each other by coupler nuts 16 and 17. A stainless steel tube 18 is affixed to and extends from one end of the Y-connector 12. A syringe plunger 20 is integral to the syringe 14. Plastic catheter tube 22 is about 100 cm long and secures to one end of the stainless steel tube 18. Annular metallic tip 24 is secured to the distal end of the plastic catheter tube 22.

A laterally movable fixation wire assembly 26 extends through and from the metallic tip 24. Fiber optic cable 30 passes through the port 28 of the Y-connector 12, the stainless steel tube 18, and the plastic catheter tube 22 and connects with the metallic tip 24. A plurality of wires, including wires 34, 36 and 38, pass through a stainless steel tube 40 which is coaxial to the syringe 14. They also pass through syringe plunger 20, the Y-connector 13, the Y-connector 12, the stainless steel tube 18 and plastic catheter tube 22, which is coupled to the annular metallic tip 24 as later described in detail.

Wire 34 is a stiffening wire and wires 36 and 38 are conductors leading to thermocouples on the fixation wire assembly 26. Another wire 32 exits the port 31 of the Y-connector 13 and connects electrically to the metallic tip 24. The port 28 of the Y-connector 12 is connected to the interior of the Y-connector 12, and more importantly, to the interior lumen of the stainless steel tube 18 and the attached plastic catheter tube 22.

A fluid is routed through the Y-connector port 28 of the Y-connector 12 along the fiber optic cable 30, through the tubes 18 and 22 and out of the annular metallic tip 24 as described later in detail. This fluid is useful in flushing and cooling the region immediately adjacent to the ablation process.

Figure 2:
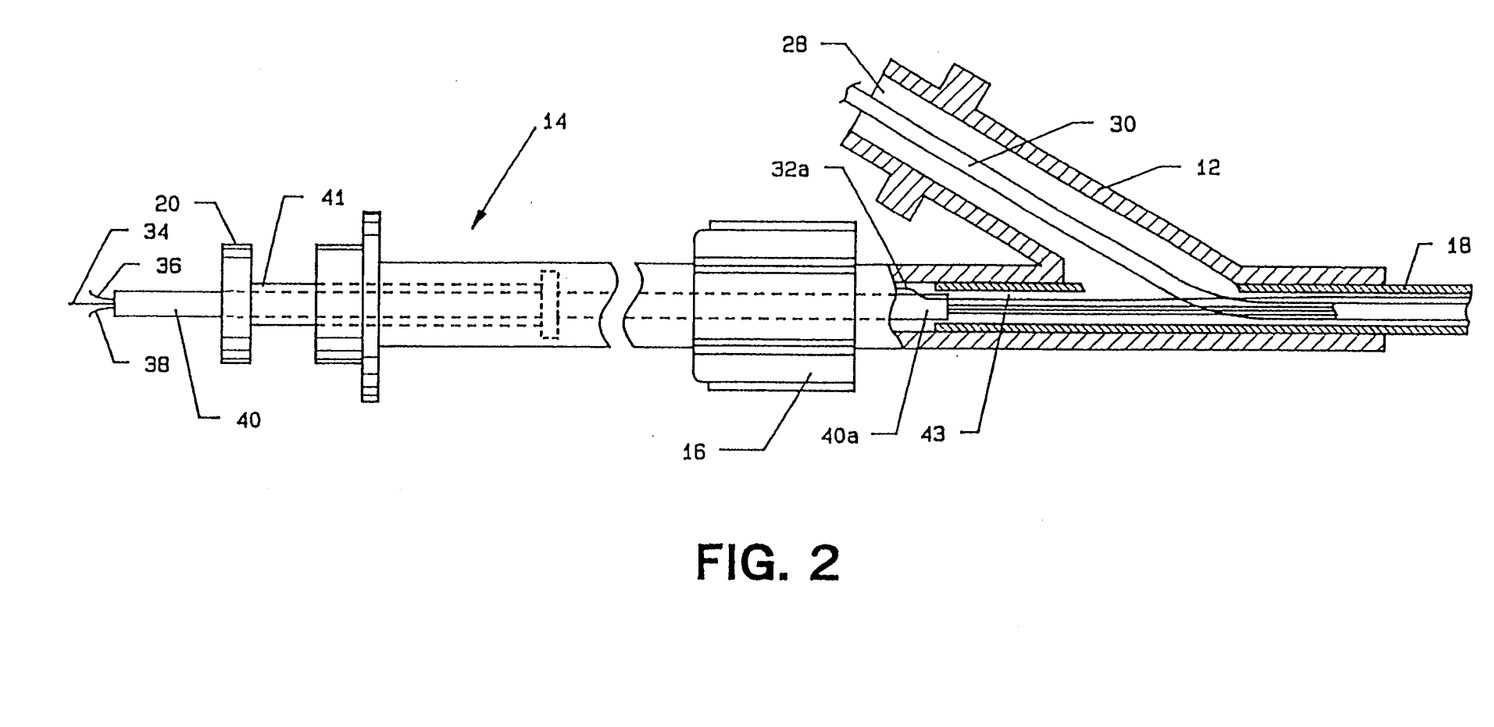
FIG. 2 illustrates a cutaway view of the syringe and Y-connector.

FIG. 2 illustrates a cutaway view of the syringe 14 and Y-connector 12 where all numerals correspond to those elements previously described. The standard features of syringe 14 are not completely illustrated for purposes of clarity and brevity. The stainless steel tube 40 aligns coaxially within and affixes to the syringe plunger tube 41. The wires 34, 36 and 38 pass through and are secured within the lumen of the stainless steel tube 40.

Distal end 40a of the stainless steel tube 40, which includes wires 34–38, slidingly aligns in the lumen 43 of the stainless steel tube 18. The fiber optic cable 30 passes through port 28 of the Y-connector 12 and into the lumen 43 of the stainless steel tube 18. Fiber optic cable 30 and the wires 32–38 share lumen 43 of the stainless steel tube 18 and pass from there into the central lumen 46 as shown in FIG. 3, of the plastic catheter tube 22.

Actuation of the plunger 20, and hence the attached stainless steel tube 40, causes the wires 34–38, which ultimately make up the majority of the structure in the fixation wire assembly 26, to move laterally as depicted by the double arrow 47 as illustrated in FIG. 1.

Figure 3:
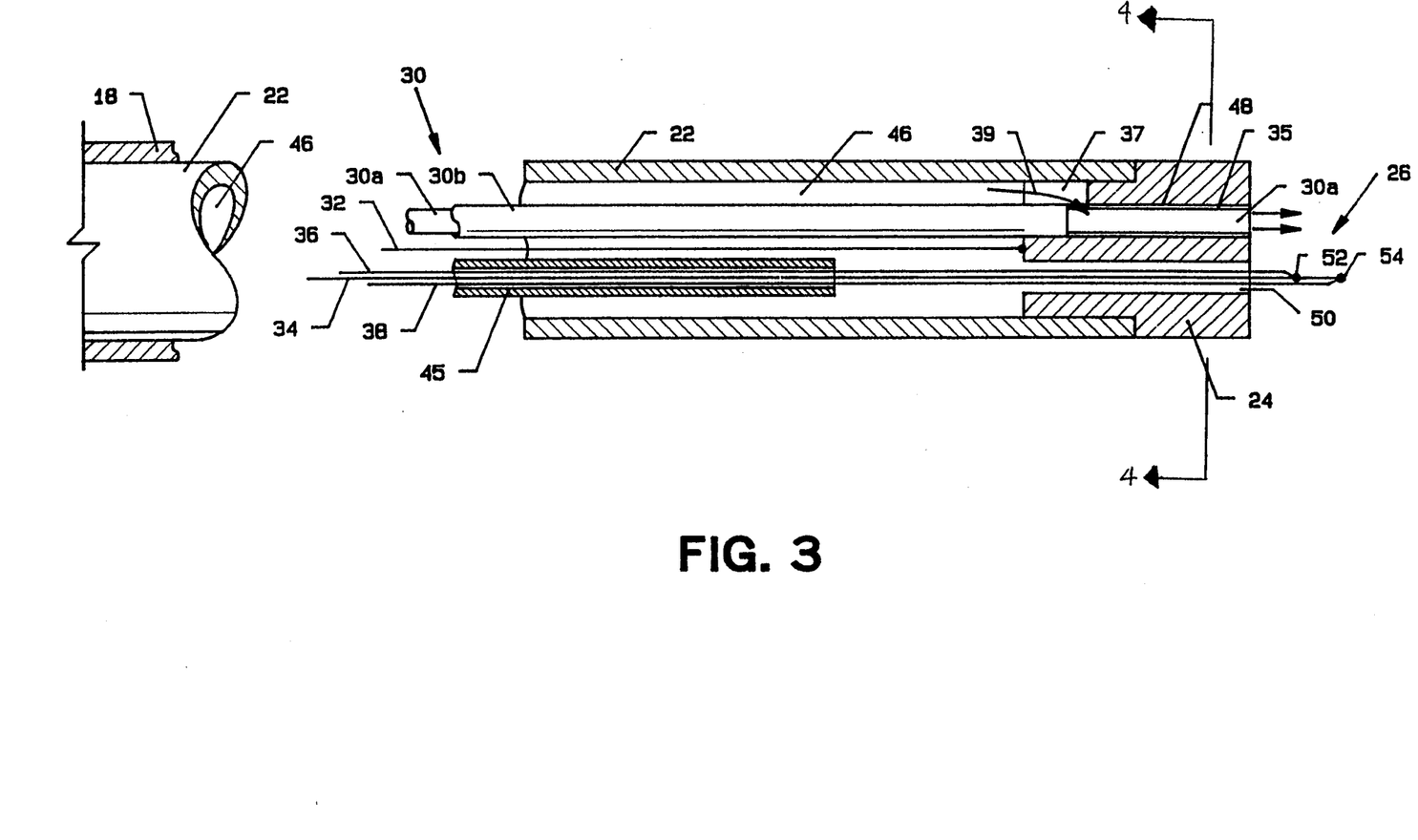
FIG. 3 illustrates a cross-sectional view of the catheter tip area along line 3—3 of FIG. 1.

FIG. 3 illustrates a cross-sectional view of the catheter tip area along line 3—3 of FIG. 1 where all numerals correspond to those elements previously described. The metallic tip 24 is multi-radiused so that the lesser radius will frictionally engage within the lumen 46 of the plastic catheter tube 22. The metallic tip 24 includes a lumen 48 for support of the distal end of the fiber optic cable 30. The fiber optic cable 30 includes the actual fiber optic core 30a coaxial with a sheath 30b. The sheath 30b is removed at the distal end to allow an annular passageway 35 to be formed between the lumen 48 and the fiber optic core 30a.

Another passageway 37 in the metallic tip 24 allows a coolant to pass as illustrated by arrow 39 from the lumen 46 through the passageway 37 and then through the annular passageway 35. Wire 32 is electrically connected to the metallic tip 24 and passes through the lumen 46 to the Y-connector 13 as previously described.

The fixation wire assembly 26 slidingly aligns in a passageway 50 in a portion of the annular metallic tip 24 and includes thermocouples 52 and 54 embedded or otherwise attached thereto. Shrink wrap tubing 45 encompasses the wires 34–38 which terminates within the stainless steel tube 18. The wires 36 and 38 connect electrically to the thermocouples 52 and 54, respectively, and are routed with the encompassing shrink wrap tubing 45 through the lumen 46 of the plastic tube 22, and to the Y-connectors 12 and 13 at the proximal end of the stainless steel tube 40 as previously described.

The fixation wire assembly 26 contains a plurality of thermocouples including the thermocouples 52 and 54 for electrical connection to one electrode of the bipolar sensing system. The metallic tip 24 provides an electrical connection for the second electrode of the electrophysiological monitoring system. The annular space between the plastic catheter tube 22 and the fiber optic cable 30 serves as a conduit for a flushing medium, such as sterile saline solution. This liquid cools the tissue and the metallic tip 24, and also removes blood from the field of laser energy during the irradiation process.

Because of the need to pass through the rather tortuous passageways of the cardiovascular system, the fixation wire assembly 26 is retracted into the metallic tip 24 during advancement of the catheter. With the fixation wire assembly 26 retracted, the distal end of the metallic tip 24 presents a very low profile device whose leading edge is smooth and free of any protrusions which would cause the catheter to hang-up during its passage through portions of the human anatomy. Upon reaching the desired position, the fixation wire assembly 26 is advanced distally by pushing syringe plunger 40 to penetrate the tissue surface. This both fixes the distal end of the catheter at the desired location and permits the temperature sensors to measure temperature at differing tissue depths.

Figure 4:
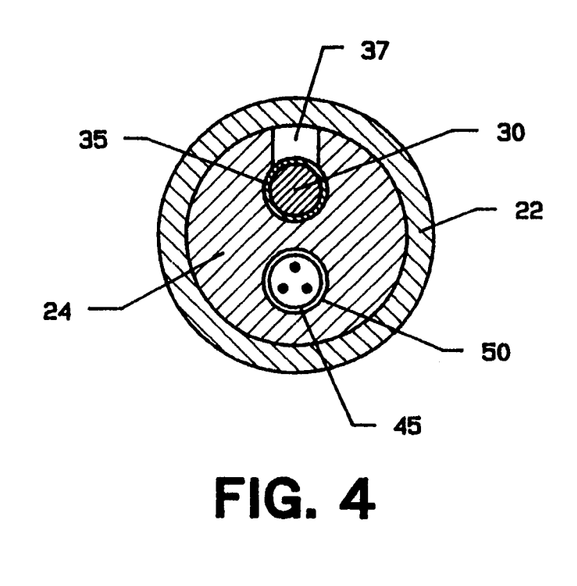
FIG. 4 illustrates a cross-sectional view along line 4—4 of FIG. 3.

FIG. 4 illustrates a cross-sectional view along line 4—4 of FIG. 3 where all numerals correspond to those elements previously described. Illustrated in particular is the fluid passageway 37. The sterile saline solution passes through the lumen 46 and through the passageway 37 to purge blood and debris from the field of view of the fiber optic cable 30 and to cool the tip 24 and adjacent tissue.

Figure 5:
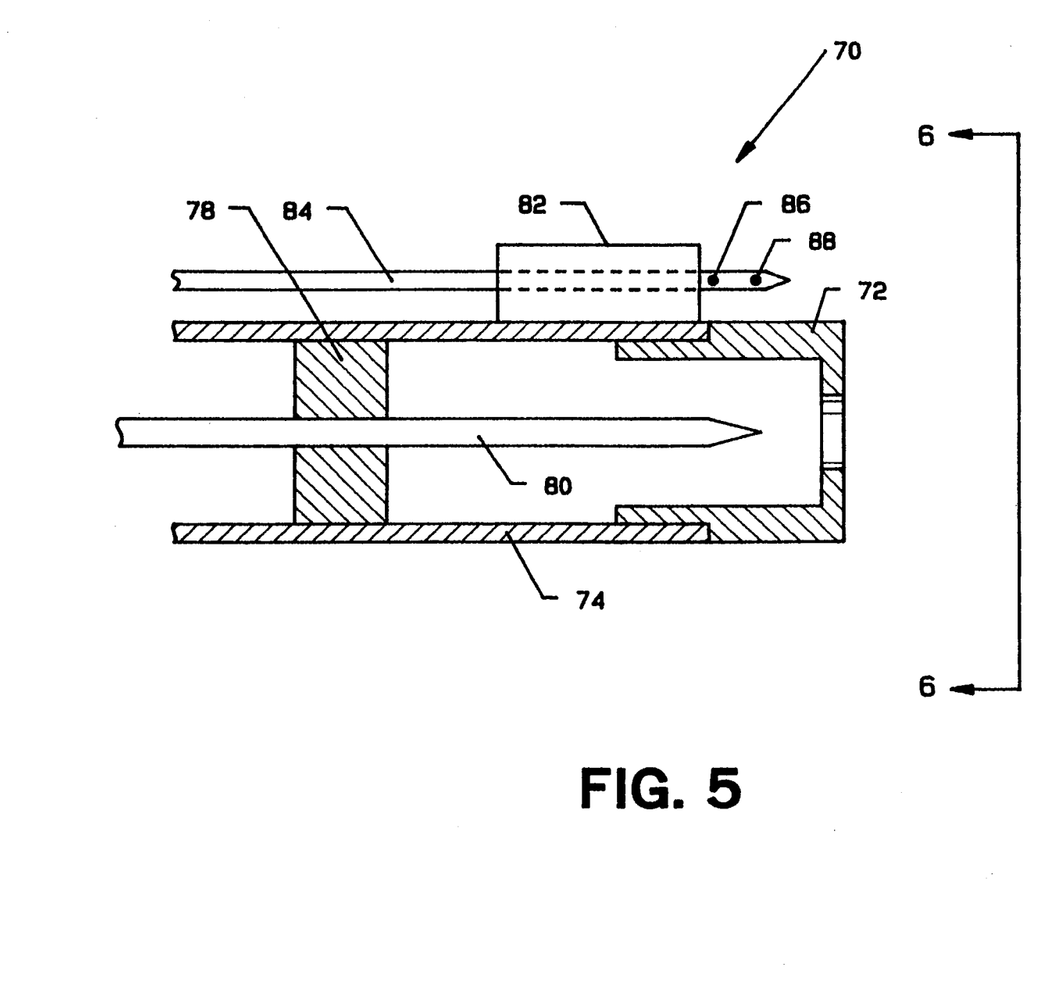
FIG. 5, an alternative embodiment, illustrates a cross-sectional view of an externally movable integral fixation wire catheter; and, FIG. 6 illustrates an end view of FIG. 5 along line 6—6.
Figure 6:
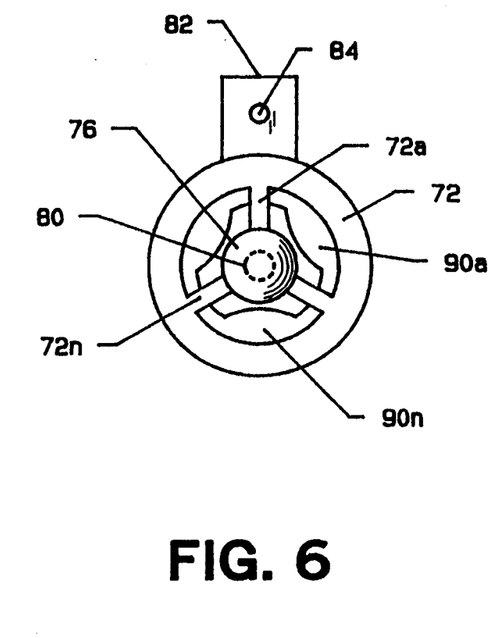

FIG. 5 is a cross-sectional view of an externally movable fixation wire catheter 70, encompassing an alternative embodiment of the present invention. Included are a lens holder 72 frictionally engaged into the distal end of a plastic catheter tube 74, a quartz lens 76 as shown in FIG. 6, secured in the lens holder 72, a spacer member 78 aligned and frictionally engaged within the plastic catheter tube 74, an optical fiber 80 aligned in the spacer member 78, a clip 82, and a fixation wire 84 aligned in the clip 82. Thermocouples 86 and 88 mount on the distal end of the fixation wire 84. The fixation wire 84 slidingly engages the clip 82, and in the alternative, may be positionally fixed within as required. In this embodiment the fixation wire along with the temperature sensors are external to, but adjacent to the main body of the catheter.

FIG. 6 illustrates an end view of FIG. 5 along line 6—6 of FIG. 5 where all numerals correspond to those elements previously described. Illustrated are the lens holder struts 72a–72n of the lens holder 72 extending inwardly to secure the quartz lens 76 in the lens holder 72. Cooling fluid passes through the passages 90a–90n between the lens skirt and the inner periphery of the lens holder 72.

Various modifications can be made to the present invention without departing from the apparent scope hereof.

We claim:

1. A laser ablation catheter for transferring laser energy from a laser generator to tissue to be ablated comprising:
   a. a catheter body of flexible body compatible material having a proximal end and a distal end;
   b. an optical fiber located within said catheter body and coupled to said laser generator at said proximal end;
   c. fixation means having a proximal end and a distal end slidably connected to said catheter body for penetrating said tissue and fixating said catheter to said tissue;
   d. a tip member on said distal end of said catheter body, said tip member having a first passageway supporting said optical fiber and a second passageway in which said fixation means is slidingly aligned; and
   e. sensing means positioned on the fixation means and on the tip member for sensing the temperature of the tissue and for measuring electrical potentials of the tissue.

2. A laser ablation catheter according to claim 1 wherein said fixation wire is located within said catheter body.

3. A laser catheter comprising:
   a. a catheter body having a proximal end, a distal end and a central lumen therethrough;
   b. an optical fiber having a proximal end and a distal end in said central lumen of said catheter body for conveying laser energy from said catheter body distal end;
   c. an axially movable tube in said catheter body extending out said catheter body proximal end;
   d. fixation means secured in and extending through said axially moveable tube for penetration of a tissue and securing said catheter to said tissue;
   e. a tip member on said distal end of said catheter body, said tip member having a first passageway supporting said optical fiber and a second passageway in which said fixation means is slidingly aligned; and
   f. sensing means positioned on the fixation means and on the tip member for sensing the temperature of the tissue and for measuring electrical potentials of the tissue.

4. The laser catheter of claim 3, wherein the sensing means comprises a plurality of thermocouples positioned along said fixation means to sense the temperature of the tissue at different depths thereof.

5. The laser catheter of claim 3 wherein said tip member has a third passageway in fluid communication with said central lumen and with said first passageway, thereby providing a coolant fluid chamber structure formed by an annular passageway structure therebetween for the flow of cooling fluid.

6. The laser catheter of claim 3 further comprising a syringe including a plunger coupled to said catheter body proximal end, and wherein said axially movable tube is coupled to said plunger.

7. A method of percutaneously guiding a laser catheter through a tortuous path in a warm-blooded animal to a tissue, said laser catheter comprising a catheter body having a proximal end and a distal end, an optical fiber having a proximal end and a distal end in said catheter body for conveying laser energy from said catheter body distal end, fixation means axially movable in said catheter body and having a proximal end and a distal end for penetrating said tissue, a tip member on said distal end of said catheter body, said tip member having a first passageway supporting said optical fiber and a second passageway in which said fixation means is slidingly aligned, and sensing means positioned on the fixation means and on the tip member for sensing the temperature of the tissue and for measuring electrical potentials of the tissue, comprising:
   a. retracting said fixation means so that said fixation means distal end is contained within said catheter body;
   b. guiding said catheter body through said tortuous path to the desired location in said warm-blooded animal;
   c. advancing said fixation wire means distally so that said fixation wire means extends out said tip member of said catheter body and penetrates a tissue surface so as to become embedded in the tissue of said warm-blooded animal so as to fix said catheter body in place.

8. The method of claim 7 wherein said laser catheter further comprises an axially movable tube in which said fixation wire is secured and through which said fixation wire extends, and wherein said fixation wire is retracted and advanced by retracting and advancing said axially movable tube.

9. A laser ablation catheter for transferring laser energy from laser generation means to tissue of a warm-blooded animal to be ablated, comprising:
   a. a catheter body having a proximal end and a distal end and a lumen therebetween;
   b. an optical fiber housed in said catheter body lumen for coupling to said laser generation means, said optical fiber having a proximal end and a distal end;
   c. fixation means having a proximal end and a distal end slidingly housed in said catheter body lumen for penetrating said tissue and securing said catheter to said tissue;
   d. a catheter tip coupled to said catheter body distal end, said catheter tip having a first lumen of a diameter larger than the outside diameter of said optical fiber distal end for supporting said distal end of said optical fiber, a second lumen for supporting said distal end of said fixation wire, and a third lumen communicating with said catheter lumen and said first lumen;
   e. a coolant fluid path in said catheter body, said path comprising a coolant fluid chamber structure formed by an annular passageway between said third lumen and said first lumen and said optical fiber distal end, the coolant fluid chamber permitting flow therethrough of a cooling fluid for cooling the catheter tip and the tissue: and
   f. sensing means positioned on the fixation means and on the catheter tip for sensing the temperature of the tissue and for measuring electrical potentials of the tissue.

10. The laser ablation catheter of claim 9, wherein said temperature sensing means comprises a plurality of thermocouples positioned along the axial length of said fixation wire.

11. The laser ablation catheter of claim 9, wherein said coolant fluid path further comprises said catheter body lumen.

12. The laser catheter of claim 3, wherein the sensing means monitors the detection and localization of tissue electrical potentials before ablation and provides feedback evaluation during ablation of said tissue.

13. The laser catheter of claim 12 wherein said sensing means comprises at least two electrodes.

14. The laser catheter of claim 1 wherein said tip member has a third passageway in fluid communication with said central lumen and with said first passageway, thereby providing a coolant fluid chamber structure formed by an annular passageway structure therebetween for the flow of cooling fluid.

15. The laser catheter of claim 1, wherein the sensing means comprises a plurality of thermocouples positioned along said fixation means to sense the temperature of the tissue at different depths thereof.

16. The laser catheter of claim 1, wherein the sensing means monitors the detection and localization of tissue electrical potentials before ablation and provides feedback evaluation during ablation of said tissue.

* * * * *

UNITED STATES PATENT AND TRADEMARK OFFICE
CERTIFICATE OF CORRECTION

PATENT NO. : 5,423,805
DATED : June 13, 1995
INVENTOR(S) : Gregory G. Brucker, et al.

It is certified that error appears in the above-indentified patent and that said Letters Patent is hereby corrected as shown below:

Col. 3, line 38, insert a comma after the numeral "46";
Col. 4, line 45, insert a comma after the numeral "76";
Col. 5, line 23, change "wire" to --means--;
Col. 6, line 22, change "wire" to --means--;
Col. 6, line 23, change the first occurrence of the word "wire" to --means--;
Col. 6, line 23, change the second occurrence of the word "wire" to --means--;
Col. 6, line 39, insert the phrase --catheter tip-- after the word "first";
Col. 6, line 42, insert the phrase --catheter tip-- after the word "second";
Col. 6, line 43, change "wire" to --means--;
Col. 6, line 43, insert the phrase --catheter tip-- after the word "third";
Col. 6, line 44, insert the word "body" after the word --catheter--;
Col. 6, line 45, insert the phrase --catheter tip-- after the word "first";
Col. 6, line 49, insert the phrase --catheter tip-- after the word "third";
Col. 6, line 49, insert the phrase --catheter tip-- after the word "first";
Col. 6, line 60, change "wire" to --means--;
Col. 7, line 5, change "said" to --a--; and
Col. 7, line 5, after the word "lumen", please insert the phrase --within said catheter body--.
Col. 7, line 3, insert "ablation" before -- catheter --.

Signed and Sealed this

Fifth Day of March, 1996

Attest:

BRUCE LEHMAN

*Attesting Officer*  *Commissioner of Patents and Trademarks*